United States Patent [19]

Bonnemain et al.

[11] Patent Number: 4,877,600
[45] Date of Patent: Oct. 31, 1989

[54] LYSINE SALT OF THE GADOLINIUM-DOTA COMPLEX AND ITS DIAGNOSTIC APPLICATIONS

[75] Inventors: Bruno Bonnemain, Mitry Mory; Jean Lautrou, Saint Mande; Dominique Meyer, Paris, all of France

[73] Assignee: Guerbet S.A., Villepinte, France

[21] Appl. No.: 141,360

[22] PCT Filed: Apr. 7, 1987

[86] PCT No.: PCT/FR87/00114
§ 371 Date: Dec. 7, 1987
§ 102(e) Date: Dec. 7, 1987

[87] PCT Pub. No.: WO87/06229
PCT Pub. Date: Oct. 22, 1987

[30] Foreign Application Priority Data

Apr. 11, 1986 [FR] France ................................ 86 05235

[51] Int. Cl.$^4$ .................. C07D 257/02; A61K 49/04; A61K 40/00
[52] U.S. Cl. ............................................ 424/4; 424/9; 514/184
[58] Field of Search ........................ 540/465; 514/184; 424/4, 9

[56] References Cited

FOREIGN PATENT DOCUMENTS 2539996 8/1984 France ................................ 314/184

Primary Examiner—Robert T. Bond
Attorney, Agent, or Firm—Young & Thompson

[57] ABSTRACT

Lysine salt of the complex of gadolinium (III) of 1,4,7,10-tetraazacyclododecane-N,N',N'',N'''-tetraacetic acid. Said salt has a low toxicity and may be used as diagnostic agent in magnetic resonance imaging.

5 Claims, No Drawings

LYSINE SALT OF THE GADOLINIUM-DOTA COMPLEX AND ITS DIAGNOSTIC APPLICATIONS

The present invention is concerned with a new salt of the gadolinium(III)-DOTA complex and its applications to diagnostics as contrast agent in magnetic resonance imaging (MRI) and in radiology by X-rays.

DOTA is the 1,4,7,10-tetra-azacyclododecane-N,N',N'',N'''-tetra-acetic acid. The H[Gd-DOTA] complex has been mentioned by J. F. Desreux in Inorg. Chem. 19, 1319, 1980. In addition, in FR-A-2 538 996, the possibility has been mentioned of using the sodium salt and the N-methylglucamine salt of this complex as diagnostic agents.

There has now been found a new salt of this complex which offers in an unexpected way a particularly low toxicity and in particular, clearly weaker than that of the N-methylglucamine salt.

The present invention has thus as its subject the lysine salt of the gadolinium(III)-DOTA complex.

This salt can be represented by the formula:

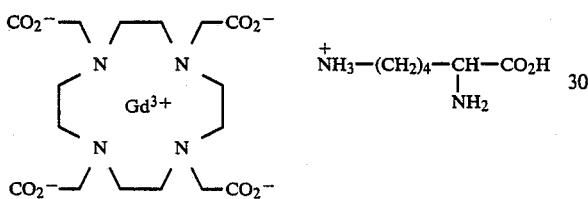

The salt according to the invention can be used as contrast agent in magnetic resonance imaging and in radiology by X-rays.

The present invention therefore also has as its subject diagnostic compositions, which can be administered to man, which include an effective amount of the lysine salt of the gadolinium(III)-DOTA complex.

The compositions according to the invention can be administered to man by parenteral (notably vascular or lymphatic), sub-arachnoid, oral or intra-bronchial route.

For administration by parenteral or oral route, the compositions according to the invention can notably be solutions of the salt in an aqueous physiologically acceptable solvent, these solutions containing notably from $10^{-5}$ mole/l to 1 mole/l of the salt. The dose which can be administered can generally be from $10^{-5}$ to $10^{-3}$ mole/kg.

For administration by intra-bronchial route, the compositions can be aerosols or suspensions.

The following examples illustrate the preparation of the salt according to the invention and compositions containing this salt.

1. Preparation of the H[GdDOTA], $H_2O$ complex 40.45 g of DOTA (0.1 mole) is added to a suspension composed of 18.13 g of gadolinium oxide $Gd_2O_3$ (0.05 mole) in 400 cm³ of distilled water.

This suspension is taken to 70° C. under agitation for 20 hours, filtered on a 0.45 μm filter, then evaporated to dryness. The resultant powder is taken up in ethyl ether, filtered, then dried under vacuum.

Analysis: ($C_{16}H_{25}N_4O_8Gd$, $H_2O$)

| Analysis: ($C_{16}H_{25}N_4O_8Gd$, $H_2O$) | C % | N % | N % |
|---|---|---|---|
| Calculated | 33.37 | 4.71 | 9.72 |
| Results | 33.31 | 4.86 | 9.82 |

2. Preparation of a solution of the lysine salt of the H[GdDOTA], $H_2O$ complex 27.93 g of the H[GdDOTA] complex is dispersed in an aqueous solution of lysine (7.91 g) at 20% by weight, by means of a magnetic agitation.

The volume is adjusted to 100 cm³ by addition of distilled water in order to obtain a solution at 0.5 mole/l.

The solution is filtered on a 0.45 μm filter, then sterilized at 120° C. for 20 minutes.

Physico-chemical characteristics of the solution

Total quantity of gadolinium (determined by atomic absorption spectrometry).

[Gd]=0.501 mole/l

Quantity of traces of non-complexed gadolinium

[$Gd^{3+}$]<0.01%

Determination of the pH.
before sterilisation ph=7.6
after sterilisation ph=7.7
No variation after 3 months at ambient temperature.
Density at 20° C.

D−1.1664

Osmolality obtained by cryoscopy at 20° C.

1400 mosm/kg.

Further on there will be given results showing the particularly weak toxicity of the salt according to the invention.

Acute toxicity by intra-venous route.

The acute toxicity has been determined on female mice (weight 20–25 g) of Swiss OF1 strain, by rapid intravenous injection (2 ml min$^{-1}$) according to the method of calculation defined by Reed and Muench in the quantal cumulative method AMJ.HYG. 27, 493, 1938. 6 animals were used per dose with a minimum of 3 doses per trial, these doses following a geometric progression. The toxicity ($LD_{50}$) is noted 7 days after the injection.

The results show a much clearer improvement in the case of the GdDOTA complex when passing from the N-methylglucamine salt to the lysine salt than in the case of the GdDTPA complex (see EP-A-0 071 564) which well shows the unexpected character of the particularly weak toxicity of the salt according to the invention.

| Complex | Salt | Solution concentration. | Volume injected | Doses injected | $LD_{50}$ mmoles/kg. |
| --- | --- | --- | --- | --- | --- |
| $H[GdDOTA]H_2O$ | N.methyl-glucamine | 0.408 mole/l. | 20–31.6 ml.kg$^{-1}$ | 8–12.9 mmoles kg$^{-1}$ | 10.9 |
| $H[GdDOTA]H_2O$ | Lysine | 0.501 mole/l. | 31.05–34.15 ml.kg$^{-1}$ | 15.5–17.1 mmoles kg$^{-1}$ | 16.6 |
| $2H[GdDTPA]$ | N.methyl-glacamine | 0.5 mole/l. | 8.16–10 ml.kg$^{-1}$ | 4.8–5 mmoles kg$^{-1}$ | 4.45 |
| $2H[GdDTPA]$ | Lysine | 0.5 mole/l. | 10–13.55 ml.kg$^{-1}$ | 5–6.7 | 5.94 |

We claim:

1. The lysine salt of the gadolinium(III) complex of 1,4,7,10-tetra-azacyclododecane-N,N',N'',N'''-tetra-acetic acid.

2. An administratable composition suitable for administration to humans as a contrast agent in magnetic resonance imaging and in radiologic X-ray imaging, said composition comprising an effective amount of the lysine salt of the gadolinium (III) complex of 1,4,7,10-tetra-azacyclododecane-N,N',N'',N'''-tetra-acetic acid.

3. The administratable composition of claim 2 comprising a solution of said salt in a physiologically acceptable aqueous solvent.

4. The administratable composition of claim 3 wherein said solution comprises from $10^{-5}$ mole/l to 1 mole/l of said salt.

5. The administratable composition of claim 2 wherein said solution comprises from $10^{-5}$ mole/kg to $10^{-3}$ mole/kg.

* * * * *